(12) United States Patent
Doroski

(10) Patent No.: US 7,954,497 B2
(45) Date of Patent: Jun. 7, 2011

(54) ARM RESTRAINT APPARATUS AND METHOD

(75) Inventor: Scott Doroski, Alexandria, VA (US)

(73) Assignee: Scott Doroski, Alexandria, VA (US)

( * ) Notice: Subject to any disclaimer, the term of this patent is extended or adjusted under 35 U.S.C. 154(b) by 838 days.

(21) Appl. No.: 11/358,442

(22) Filed: Feb. 22, 2006

(65) Prior Publication Data

US 2007/0193589 A1 Aug. 23, 2007

(51) Int. Cl.
*A61F 5/37* (2006.01)
(52) U.S. Cl. ......................................................... 128/878
(58) Field of Classification Search .................. 482/20, 482/50, 93, 121, 125, 907; 128/869, 878
See application file for complete search history.

(56) References Cited

U.S. PATENT DOCUMENTS

| | | | | | |
|---|---|---|---|---|---|
| 4,414,969 | A | * | 11/1983 | Heyman | 128/878 |
| 4,422,455 | A | * | 12/1983 | Olsen | 128/878 |
| 4,905,713 | A | * | 3/1990 | Morante | 128/875 |
| 5,188,365 | A | * | 2/1993 | Picard | 473/213 |
| 5,345,947 | A | * | 9/1994 | Fisher | 128/878 |
| 5,348,292 | A | * | 9/1994 | Norman, Sr. | 473/438 |
| 5,397,122 | A | * | 3/1995 | Herridge, II | 473/212 |
| 5,507,046 | A | * | 4/1996 | Taylor | 5/414 |
| 5,551,379 | A | * | 9/1996 | Hart | 119/771 |
| 5,704,856 | A | * | 1/1998 | Morse | 473/422 |
| 5,829,443 | A | * | 11/1998 | Cunningham | 128/869 |
| 5,893,366 | A | * | 4/1999 | Odell et al. | 128/869 |
| 6,299,569 | B1 | * | 10/2001 | Rich | 482/123 |
| 6,773,366 | B2 | * | 8/2004 | Gray | 473/458 |
| 6,874,506 | B2 | * | 4/2005 | Chapman | 128/869 |
| 2002/0092531 | A1 | * | 7/2002 | Chapman | 128/878 |
| 2004/0152569 | A1 | * | 8/2004 | Lerner | 482/124 |
| 2006/0229175 | A1 | * | 10/2006 | Frappier | 482/124 |

* cited by examiner

Primary Examiner — Kristen C Matter

(57) ABSTRACT

An arm restraint for restricting movement of a person's arm during sleep. The arm restraint includes a lower strap, an extension part coupled to the lower strap at one end of the extension part, the extension part including an adjusting unit for adjusting a length of the extension part, and an upper strap coupled to the extension part at another end of the extension part. The lower strap is wrapped around a lower part of a person's body. The upper strap is wrapped around an arm of the person's body. The extension part is sized by way of the adjusting unit such that the arm cannot abduct above a shoulder level of the person.

4 Claims, 2 Drawing Sheets

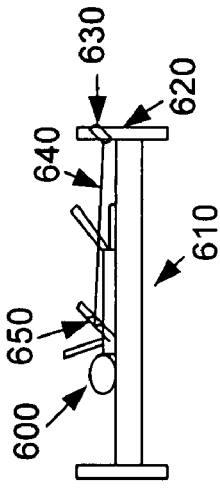
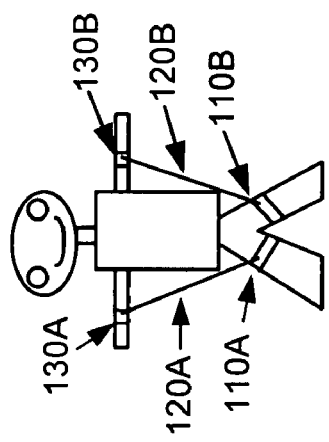
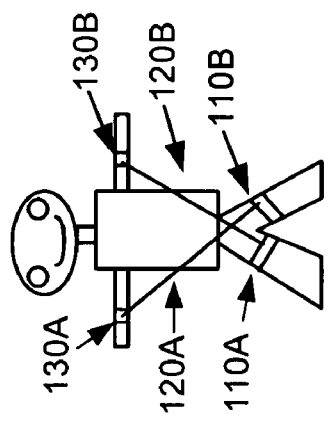

ARM RESTRAINT APPARATUS AND METHOD

BACKGROUND OF THE INVENTION

The present invention relates to an apparatus and method for alleviating shoulder pain that may occur do to movements of a person at night, during sleep. In particular, the present invention relates to a strap that keeps a person's arm from abducting above the shoulder during sleep.

DESCRIPTION OF THE RELATED ART

Many persons complain of shoulder pain that occurs due the person's arm abducting above his/her shoulder during sleep. Some doctors and chiropractors recommend that a person grasp his/her pillow prior to sleeping, so as to keep the arm in a preferred position beneath the shoulder. However, this method is not foolproof, since a person tends to toss and turn during sleep, which may involve releasing the grasp of the pillow, thereby allowing one or both arms to abduct above the shoulder. With the arm in such a position during sleep, this tends to cause shoulder pain for a person, which can be difficult to treat.

The present invention is directed to solving such a problem.

SUMMARY OF THE INVENTION

One aspect of the invention relates to an arm restraint. The arm restraint includes a lower strap, an extension part coupled to the lower strap at one end of the extension part, the extension part including an adjusting unit for adjusting a length of the extension part, and an upper strap coupled to the extension part at another end of the extension part. The lower strap is wrapped around a lower part of a person's body. The upper strap is wrapped around an arm of the person's body. The extension part is sized by way of the adjusting unit such that the arm cannot abduct above a shoulder level of the person.

Another aspect of the invention relates to a method of restraining arm movement of a person during sleep. The method includes fitting an upper strap of an arm restraint to an arm of the person. The method also includes fitting a lower strap of the arm restraint to a lower body portion of the person, or to a fixedly positioned object adjacent to the lower body portion of the person. The method further includes adjusting a size of an extension portion that is coupled at one end to the upper strap and that is coupled at another end to the lower strap, so that the arm of the person cannot abduct above a shoulder level of the person.

Other features and advantages of the present invention will become apparent to those skilled in the art from the following detailed description and accompanying drawings. It should be understood, however, that the detailed description and specific examples, while indicating preferred embodiments of the present invention, are given by way of illustration and not limitation. Many modifications and changes within the scope of the present invention may be made without departing from the spirit thereof, and the invention includes all such modifications.

BRIEF DESCRIPTION OF THE DRAWINGS

The exemplary embodiments will hereafter be described with reference to the accompanying drawings, wherein like numerals depict like elements, and:

FIG. 4 shows an arm restraint according to another embodiment of the invention, which includes a left side arm restraint and a right side arm restraint.

FIG. 5 shows an arm restraint according to yet another embodiment of the invention, which includes two arm restraints that cross each other on a person's body.

FIG. 6 shows an arm restraint according to an embodiment of the invention, which has one strap coupled to a person's arm and another strap coupled to a bed post of a bed on which a person is positioned.

DETAILED DESCRIPTION OF THE PREFERRED EMBODIMENTS

In the following description, for the purposes of explanation, numerous specific details are set forth in order to provide a thorough understanding of the present invention. It will be evident to one skilled in the art, however, that the exemplary embodiments may be practiced without these specific details. In other instances, structures and device are shown in diagram form in order to facilitate description of the exemplary embodiments.

Figure 1:
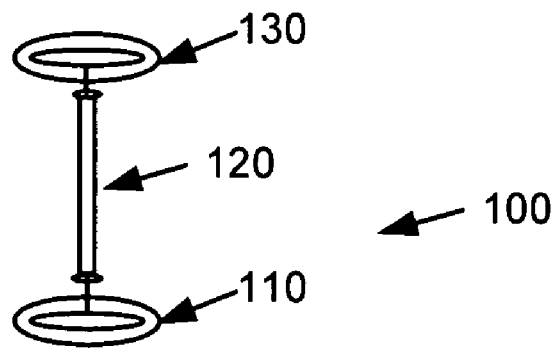
FIG. 1 shows an arm restraint according to a first embodiment of the invention.

FIG. 1 shows a shoulder pain alleviating device according to a first embodiment of the invention. The device 100 includes a lower strap 110, an extension part 120 coupled to the lower strap at a lower end of the extension part 120, and an upper strap 130 that is coupled to the extension part 120 at an upper end of the extension part 120. The lower strap 110 is preferably fitted around a person's left or right thigh region, and may include a VELCRO™ pad on both ends of the lower strap 110, so that the lower strap 110 can be sized to fit a particular person's thigh or ankle in a snug (but not too tight) manner.

With the lower strap 110 fitted in place around a person's thigh, the upper strap 130 is then fitted around the person's wrist that is on the same side of the body as the thigh on which the lower strap 110 is fitted. The upper strap 130 may include a VELCRO™ pad or other type of mechanical attachment and deattachment unit (e.g., snap fit male and female components) provided on both ends of the upper strap 130, so that the upper strap 130 can be sized to fit a particular person's wrist in a snug (but not too tight) manner. The upper strap 130 may be fitted on either an upper arm portion of a lower arm portion of the person's arm or around the person's wrist, depending on which is the most comfortable position for allowing the person to be able to sleep with the device 100 coupled to the person. The closer the upper strap 130 is positioned to the person's wrist, the more restriction of movement above the level of the person's shoulder is provided by way of the device 100.

With the upper strap 130 and the lower strap 110 positioned on the person's arm and thigh or ankle, respectively, the extension part 120 is sized so as to not allow the person's arm to abduct greater than 45 degrees from the body. The extension part 120 may correspond to a leather strap similar to a belt strap, and may include a sizing mechanism to allow the extension part 120 to be sized to fit a particular person's torso (e.g., distance from thigh or ankle to arm). For example, the extension part 120 may include holes similar to a belt, to allow a person to size the extension part 120 such that, when the lower strap 110 is wrapped around the person's thigh, the person's arm (with the upper strap 130 wrapped therearound) cannot abduct past 45 degrees from the body.

The coupling of the upper strap 130 to the extension part 120 and the coupling of the lower strap 110 to the extension part 120 may be by way of a pivotable mechanism, to allow 360 degree of movement of the extension part 120 with respect to the upper strap 130 and the lower strap 110. The pivotable mechanism may be a metal or a plastic part, or a combination thereof. Other couplings may be envisioned, while remaining within the spirit and scope of the invention.

The lower strap 110 may be wrapped around the person's upper or lower thigh, depending upon which location provides the best comfort to the person so as to allow the person to have a restful sleep with the device 100 coupled to the person. Depending upon the location which the lower strap 110 is wrapped around the person's body, the extension part 120 is increased or decreased in size so a particular size so as to prevent the person's arm (with the upper strap 130 wrapped therearound) from abducting greater the 45 degrees from the body.

Figure 2:
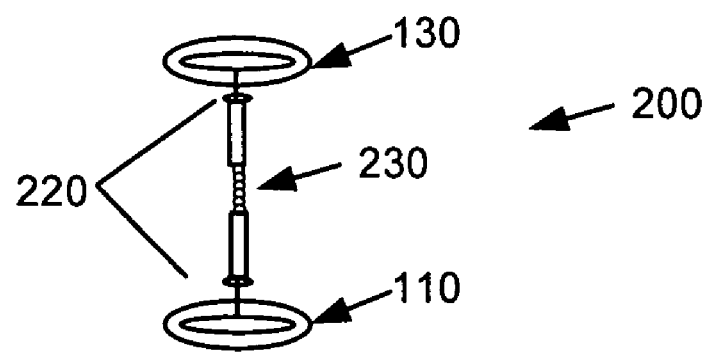
FIG. 2 is shows an arm restraint according to a second embodiment of the invention.

FIG. 2 shows a device 200 according to a second embodiment of the invention, whereby the device has an upper strap 130 and a lower strap 110 similar to the description above with respect to the first embodiment, but whereby the extension part 220 is different from the first embodiment in that the extension part 220 includes a stretchable portion 230 that allows the extension part 220 to be extended a particular amount (e.g., 2 to 5 inches). For example, the stretchable portion 230 may correspond to a bungee cord or a flexible rubber section, whereby the entire extension part 220 may correspond to a bungee cord or flexible rubber section in an alternative implementation of the second embodiment. With such an extension part 220 that is stretchable, a person does not have to precisely size the extension part 220 to suit a particular person's torso; rather, the extension part 220 has some 'give' to it, to allow it to be used for all types of persons, short and tall.

Also, the stretchable nature of the extension part 220 allows a person to be able to move his/her arm to a certain extent during sleep, without bothering the person, and without causing any stress on the upper strap 130 and the lower strap 110. The stretchability of the extension part 220 is such that the person's arm cannot abduct above the shoulder level, which prevents the person from placing his/her arm in a position that may result in shoulder pain upon awaking from sleeping in such a undesirable position.

Instead of using Velcro pads for coupling the lower strap 110 and the upper strap 130 around a person's body (or around a fixed object for the lower strap 110 in certain implementations), other types of mechanical affixing devices, such as snap-fitted tabs, a button-and-hole coupling, or belt-like components with holes on one end and with a coupler on another end, may be utilized. FIG. 6 of the drawings shows the lower strap 630 fitted around a bed post 620 of a bed 610 on which a person 600 is positioned, whereby the upper strap 650 is fitted over the person's arm (with an extension part 640 connecting the upper strap 650 with the lower strap 630). In this case, the bed post 620 of the bed 610 corresponds to the "fixed object" that the lower strap is coupled to, as discussed above.

Each of the components making up the device 100 or the device 200 is preferably a cloth or leather component, which provides a comfortable fit to a person when that part is in contact or close to the person's body. These components are preferably sturdy enough so that they don't break or rip when a person moves his/her arms and/or legs during sleep.

Figure 3:
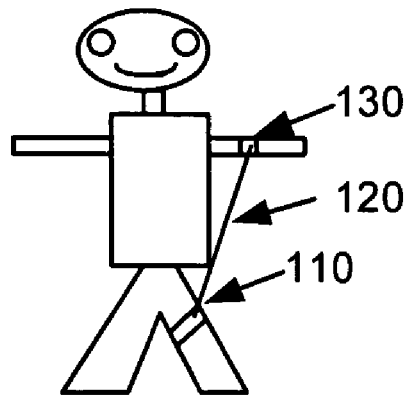
FIG. 3 shows an arm restraint according to an embodiment of the invention provided on a person to restrain that person's arm movements during sleep.

FIG. 3 shows an uppermost allowable position of a person's arm during sleep, with the device 100 or 200 attached to the person, whereby the person's arm cannot abduct above the level of the person's shoulder. This provides a preferable sleeping position so that the person will not experience shoulder pain due to the person's arm abducting too far upwards during sleep.

Depending upon the person and the pain that person may have experienced in the past, a device 100 or 200 may be provided on each side of the person, whereby one device 100 or 200 has a lower strap 110A wrapped around the person's left thigh and an upper strap 130A wrapped around the person's left arm, and whereby another device 100 or 200 has a lower strap 110B wrapped around the person's right thigh and an upper strap 130B wrapped around the person's right arm, and with two extension parts 120A, 120B respectively provided between the upper and lower straps, as seen in FIG. 4. In an alternative implementation, a person may choose to cross over his/her body and wrap a lower strap 110 around a lower left region of his/her body and wrap an upper strap 130 around his/her right arm, or vice versa. FIG. 5 shows the "cross over" implementation.

In a third embodiment, a second extension part (not shown) is pivotably coupled (by way of another pivotable mechanism, or the same pivotable mechanism used to couple the first extension part) to the lower strap 110, whereby the second extension part has a second upper strap pivotable coupled at the other end of the second extension part. With such a device, a person can restrict movement of both his arms and shoulders so that they do not move above the level of the person's shoulder. The person will size the two extension parts in such a manner to restrict movement of the person's arms and shoulders accordingly. Either or both of the first and second extension parts may be partially or totally or non-stretchable, as discussed above with respect to the second embodiment. The pivotable couplings allow for the extension part to be easily moved to either on top of the person's body during sleep, beneath the person's body during sleep, or to the side of the person's body during sleep.

Many other changes and modifications may be made to the present invention without departing from the spirit thereof. The scope of these and other changes will become apparent from the appended claims.

What is claimed is:

1. An arm restraint, comprising:
 a first lower strap that is adapted to be wrapped around a right leg of a person's body;
 a first extension part coupled to the first lower strap at one end of the first extension part, the first extension part including an adjusting unit for adjusting a length of the first extension part;
 a first upper strap coupled to the first extension part at another end of the first extension part;
 a first pivoting unit provided between the first lower strap and the first extension part, for allowing the first extension part to move 360 degrees with respect to the first lower strap; and
 a second pivoting unit provided between the first upper strap and the first extension part, for allowing the first extension part to move 360 degrees with respect to the first upper strap;
 a second lower strap that is adapted to be wrapped around a left leg of the person's body;
 a second extension part coupled to the second lower strap at one end of the second extension part, the second extension part including a second adjusting unit for adjusting a length of the second extension part; and a second upper strap coupled to the second extension part at another end of the second extension part, wherein the second upper strap is adapted to be wrapped around a right arm of the person's body, wherein the first upper strap is adapted to be wrapped around a left arm of the person's body, wherein the first extension part is sized by way of the adjusting unit such that the arm cannot abduct above a shoulder level of the person's body, and wherein the first extension part includes a stretchable portion that allows the first extension part to be increased in length by an outward force provided on one or both ends of the first extension part, and wherein the first extension part includes a first non-stretchable portion provided between the stretchable portion and the first upper strap, and a second non-stretchable portion provided between the stretchable portion and the first lower strap.

2. The arm restraint according to claim 1, wherein the first and second upper straps and the first and second lower straps each include size adjusting means for sizing the first and second upper straps and the first and second lower straps to snugly fit around a body part or an object.

3. The arm restraint according to claim 1, wherein the arm cannot abduct past 45 degrees from the person's body when the arm restraint is coupled to the person's body.

4. The arm restraint according to claim 1, wherein the arm restraint is configured to provide a comfortable fit on the person's body.

* * * * *